United States Patent [19]

Carrell et al.

[11] Patent Number: 5,066,277
[45] Date of Patent: Nov. 19, 1991

[54] PROTECTIVE SYSTEM FOR SAFE DISPOSITION OF A HYPODERMIC SYRINGE DEVICE

[75] Inventors: Michael W. Carrell; Stephen H. Gericke, both of Oklahoma City, Okla.

[73] Assignee: Safe Medical Devices, Inc., Moore, Okla.

[21] Appl. No.: 652,521

[22] Filed: Feb. 8, 1991

Related U.S. Application Data

[63] Continuation of Ser. No. 550,328, Jul. 9, 1990.

[51] Int. Cl.$^5$ ............................................. A61M 5/00
[52] U.S. Cl. ...................................... 604/110; 604/195
[58] Field of Search ............... 604/110, 195, 187, 198, 604/263

[56] References Cited

U.S. PATENT DOCUMENTS

| | | |
|---|---|---|
| 2,571,653 | 10/1951 | Bastien . |
| 2,674,246 | 4/1954 | Bower . |
| 2,845,065 | 7/1958 | Gabriel . |
| 4,631,057 | 12/1986 | Mitchell ............................... 604/198 |
| 4,655,751 | 4/1987 | Harbaugh ............................. 604/198 |
| 4,664,653 | 5/1987 | Sagstetter et al. ................... 604/197 |
| 4,710,170 | 12/1987 | Haber et al. ......................... 604/110 |
| 4,737,144 | 4/1988 | Choksi ................................. 604/198 |
| 4,738,663 | 4/1988 | Bogan ................................. 604/198 |
| 4,846,796 | 7/1989 | Carrell et al. ....................... 604/110 |

*Primary Examiner*—John D. Yasko
*Attorney, Agent, or Firm*—Laney, Dougherty, Hessin & Beavers

[57] ABSTRACT

A device for protectively sheathing a syringe and hypodermic injection or body fluid withdrawal element, which device includes a tubular sheath having a syringe barrel reciprocably mounted within the tubular sheth for coaxial movement. The barrel carries a plunger for moving a liquid through a spout or tip on one end of the barrel. The sheath, near one of its ends, carries a locking element, and the barrel, adjacent its end through which liquid passes upon reciprocation of the plunger, carries a cooperating locking element which interlocks with that locking element carried by the sheath when the barrel is withdrawn into the sheath to a location where the barrel tip is totally encased and any hypodermic injection or fluid withdrawal element which is carried on the tip of the barrel is protected.

7 Claims, 2 Drawing Sheets

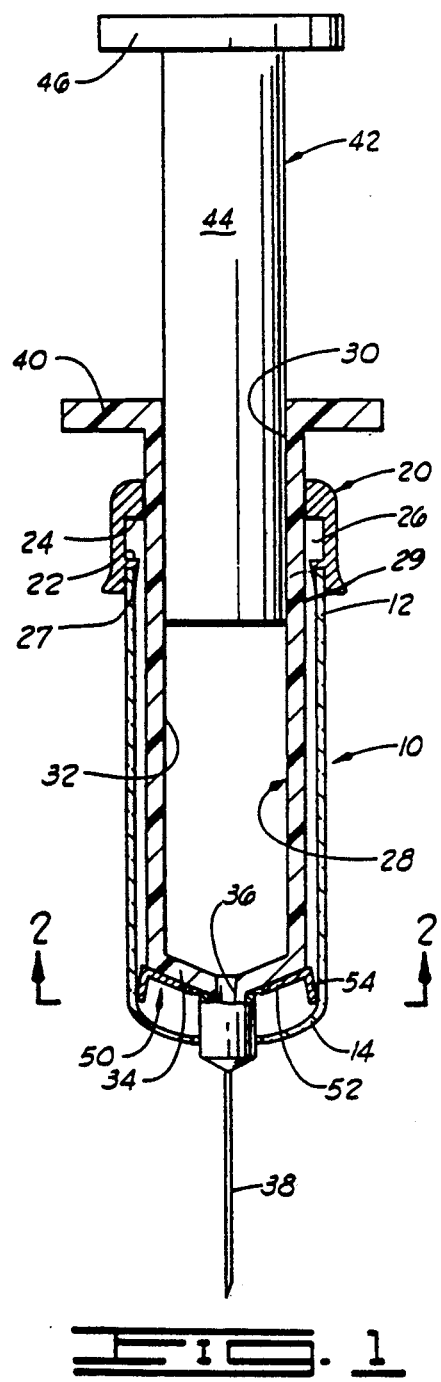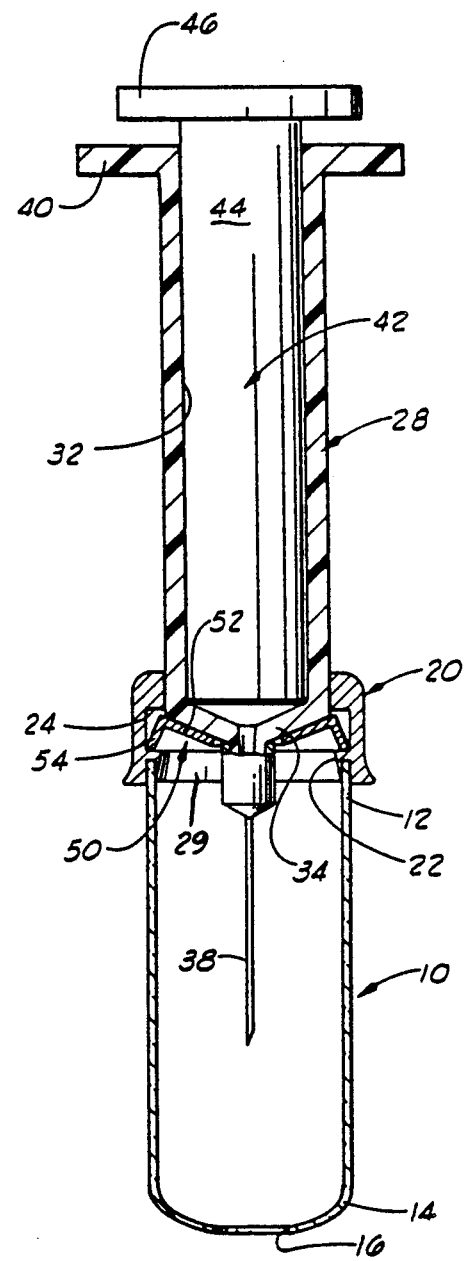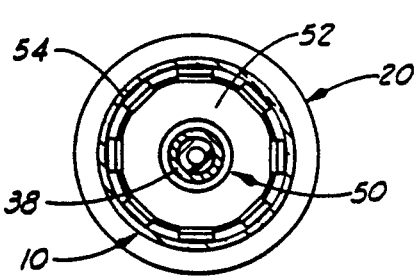

PROTECTIVE SYSTEM FOR SAFE DISPOSITION OF A HYPODERMIC SYRINGE DEVICE

This is a continuation of copending U.S. Pat. application Ser. No. 7/550,328 filed on Jul. 9, 1990, pending.

BACKGROUND OF THE INVENTION

1. Field Of The Invention

This invention relates to a device which locks the ejection tip of a hypodermic syringe and a hypodermic needle carried thereon within a protective shield, so that the needle can be safely discarded, and unauthorized re-use thereof is prevented.

2. Brief Description of The Prior Art

In the medical knowledge and understanding of various communicable diseases of the present day, it is well understood that the blood may carry viruses or microbial entities which are active instrumentalities in the transmission of disease from one individual to another. Blood which is thus "contaminated" must therefore be limited in its susceptibility to human contact outside the body of the carrier so that the exposure of medical personnel or others who may be in close association with the carrier of the communicable disease is minimized. In situations, for example, where the carrier is a patient and the medical procedure being performed requires exposure to the patient's blood, it may be important that no contact of the blood of the patient with the physician or other medical personnel occurs.

One frequently performed medical procedure involves piercing the skin of the patient to administer hypodermic injections of medicaments or nutrients, or to extract body fluids for analysis and testing. This procedure poses a risk of transmission of communicable disease through the contact of the blood or body fluids of the patient with medical personnel, or the inadvertent introduction of a miniscule amount of such blood or body fluids into the blood stream of such personnel (through a scratch, exposed abrasion or the like).

An especially intense concern has recently arisen in the case of the disease called "acquired immune deficiency syndrome" (AIDS) because it is well known that this disease is transmitted with the blood of an infected person, and because of the fact that the disease, without presently known exception, is fatal when contracted. Because of the rapid, near epidemic spread of the AIDS disease and the knowledge that one source of contraction of the disease is contaminated blood, it has become a great concern that hypodermic needles and syringes used for drawing blood, or for injecting medicaments or the like into the body of a patient for medical or dental purposes, be used only once, and then disposed safely and with finality, so that personnel may not inadvertently use the same needle for a second injection, or for withdrawal of body fluids, or may not become inadvertently and accidentally scratched by the exposed point of such a once used hypodermic needle, or contaminated by body fluids exposed upon the barrel or tip of the syringe.

It is also understood, from the concerns of medicine with the transmission of various social diseases, and with the arresting and reversal of the wide spread practice of drug abuse, that the repeated use of inadequately cleaned hypodermic needles by persons who abuse drugs of the type which are taken intravenously and by subcutaneous injection poses a real threat of the transmission of certain social diseases, including AIDS, from one person to another. Persons who are addicted to the use of drugs taken intravenously generally utilize syringes and hypodermic paraphernalia for accomplishing various injections of such drugs into the blood stream. Because of the frequent disregard of such persons for the cleanliness or the source of hypodermic needles and syringes used for practicing their habit, it is highly desirable that hospitals, clinics and other places where great numbers of hypodermic syringes and needles are to be used and then discarded take great care in the disposal of these devices. These devices should be discarded in a way such that they cannot be picked up and re-used by such persons who are careless in such use, and who may lack adequate funds or motivation to procure new and medically sterile syringes for the purpose of practicing such drug injection habits.

Recently, strict rules and procedures have been placed in effect which undertake to assure that hypodermic needles and syringes and hypodermic injection devices used in hospitals and clinics are disposed of in a way which prevents their re-use, and assures that they are safe from inadvertent contact.

Various devices and apparatus have been proposed for securing and for shielding the tip and body of a syringe and hypodermic needle from view and from contact prior to actual use. For example, in Gabriel U.S. Pat. No. 2,845,065, a flexible and resilient element in the form of a sleeve or tubular element is placed over the hypodermic needle carried at the lower end of the syringe barrel. This sleeve is forced, by contact with the body, at the time of a hypodermic or subcutaneous injection, to move toward the syringe barrel in a direction which allows the needle to become exposed, and to penetrate the body. Prior to this time, and even at this time, the needle has not been visually perceptible, and may remain invisible because of the extension of the sleeve to the point of injection, at which point the sleeve bears against the skin and surrounds the point where the needle pierces the skin.

This device is, of course, constructed in this way primarily to prevent those who have a phobia about the use of needles for administering hypodermic injections from being as alarmed or frightened as would otherwise be the case if the needle were in full view. Such devices, after functioning to hide the needle until the time of injection, can be returned to a shielding position where the needle is again surrounded and obscured from view following the injection. The very nature of such flexible and resilient sleeves which permit them to be forced back with little pressure from the body when a shot is to be given, and the sleeve contacts the body, also prevents such a sleeve from affording any very significant protection for the needle because such sleeve can be easily forced back to a position where the needle can be inadvertently contacted, and can even be re-used if such is attempted.

Another device which is intended to hide from view the needle associated with the hypodermic syringe until the instant of injection is depicted and described in U.S. Pat. No. 2,571,653 to Bastien. In the Bastien patent, a syringe is provided which is a conventional hypodermic syringe, but which is fitted with a concealing tubular sheath fitted over one end of the barrel. The sheath is slidable along the barrel between two positions to which it is indexed by means of a small latch which projects through the side of the sheath and consecutively engages a pair of grooves formed in the outer surface of the syringe barrel at axially spaced locations.

In the use of the Bastien syringe, the person who is to administer an injection with the syringe initially fills the syringe with a medicament to be injected, and then places the sheath over the lower end of the barrel so that the latch is engaged with the lower of the annular grooves formed around the barrel. The sheath at this time obscures or prevents view of a needle carried on the lower end of the barrel.

When the injection is administered, the person administering the injection pulls a handle of the sheath and pushes a handle of the barrel, so that the two move relatively toward each other, thus causing the sheath to move upwardly along the barrel until the latch enters the second groove. At this time the needle is exposed and the injection can be given. This procedure is reversible so that the sheath can be re-set to an obscuring, or view-blocking position, if desired, thus permitting the syringe to be re-used any number of times desired. The latch is made so it can be easily popped in and out of either of the annular grooves in the barrel simply by the operator's finger pressure. The Bastien device therefore does not afford any significant protection against re-utilization of the syringe and the needle which it carries, and against consequent contamination of any unauthorized users or persons who may inadvertently become scratched by the exposed needle.

Another deficiency of the Bastien device as a protective assembly which cannot be easily moved to a position in which access can be had to the needle is that the mechanism which effects the temporary latching is exposed on the outer side of the sheath, and can therefore be easily destroyed or rendered inoperative by anyone. Little or no significant force or strength is required to do so to effect the unlatching of the barrel from the sheath.

A hypodermic syringe assembly which temporarily protects or covers the needle of the syringe is shown in Bower U.S. Pat. No. 2,674,246. Here, however, the principal objective of the Bower hypodermic syringe construction is simply to conceal the needle from a patient until the instant of injection. The concealing tubular member or guide which surrounds the needle is spring biased outwardly to a position where it will hide the needle from view. Finger pressure on the barrel of the syringe is sufficient, however, to overcome the bias of the spring, and to cause the needle to be extended out the end of the protective sleeve or tube and through the skin of the patient. There is therefore no safe position which precluded unauthorized use of the needle, and indeed, merely dropping the device would apparently cause its spring to be compressed sufficiently to permit the needle to scratch the skin if it should inadvertently fall against the leg or foot of a person.

Another manually operable syringe device which obscures or hides the needle from view prior to use of the needle is that which is shown in Sagstetter U.S. Pat. No. 4,664,653. The Sagstetter injection apparatus is, however, intended to be reusable, and the entire syringe unit can be removed from the protective housing following the administration of the initial injection. After such removal, the needle is covered only by a flexible, easily penetrable sleeve.

GENERAL DESCRIPTION OF THE PRESENT INVENTION

The present invention provides a system for protectively sheathing a syringe and hypodermic injection element, such as a hypodermic needle, which protective system includes a tubular sheath which has a syringe barrel reciprocably, coaxially and concentrically mounted within the tubular sheath for coaxial movement therewithin. The barrel reciprocably receives a plunger in conventional fashion, and the plunger is functional to eject a liquid from a spout or tip on one end of the barrel.

The sheath, near one of its ends, carries a locking element, and the barrel, adjacent its end through which liquid is ejected upon reciprocation of the plunger, is connected to a second and cooperating locking element. The latter locking element functions to interlock with the first-described locking element carried by the sheath at a time when the barrel has been retracted or withdrawn into the sheath to a location therewithin where the barrel tip through which the liquid is ejected is totally encased within the sheath, and is protected by it. The interlock is such that it cannot be inadvertently, nor indeed easily, broken or displaced. The syringe and/or needle, protected in this way, can therefore be discarded without fear of re-use or inadvertent scratching or puncturing of the flesh of persons with whom it might otherwise accidentally come into contact.

An important object of the invention is to provide a protective system or assembly which includes a protective tubular sheath which, following the administration of an injection, or the hypodermic or subcutaneous introduction of a medicament into the body, or the withdrawal of a body fluid, can be used to render the syringe device completely inoperative, and to protect the syringe and/or any hypodermic injection device, such as a needle, which it may carry, from inadvertent or careless contact by individuals who may be in close proximity to the system. Further the protective system or assembly permits discard or disposal of used syringes and needles without fear for their subsequent reuse by unauthorized personnel.

Additional objects and advantages of the invention will become apparent as the following detailed description of a preferred embodiment of the invention is read in conjunction with a perusal of the accompanying drawings which illustrate such preferred embodiment.

GENERAL DESCRIPTION OF THE DRAWINGS

FIG. 1 is a view partially in side elevation and partially in longitudinal section of a protective device constructed in accordance with the present invention. The device is illustrated at a time when the device is in a status in which it can be used for administering a hypodermic injection.

FIG. 2 is a view taken along line 2—2 of FIG. 1.

FIG. 3 is a view partially in section and partially in side elevation, similar to FIG. 1, but showing the protective device in a safe, throw-away status in which the hypodermic injection syringe assembly has been withdrawn into the protective sheath and locked therein so as to protect the hypodermic needle carried on one end of the syringe.

DETAILED DESCRIPTION OF A PREFERRED EMBODIMENT OF THE INVENTION

Figures 4A, 4B, 4C:
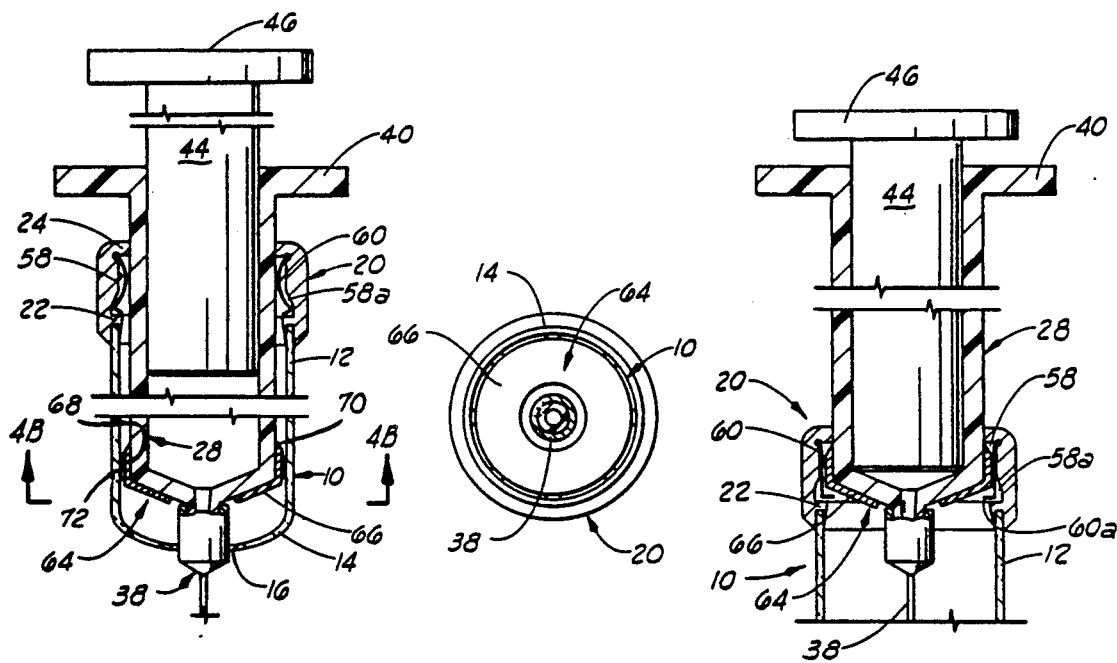
FIG. 4A is a view partially in section and partly in elevation, similar to FIG. 1, but having parts broken away, and illustrating a different embodiment of the invention from that which is illustrated in FIGS. 1-3. The status of the protective system illustrated in FIG. 4A is that of the system at the time it is used for administering a hypodermic injection.
FIG. 4B is a sectional view taken along line 4B—4B of FIG. 4A.
FIG. 4C is a view partially in section and partially in side elevation illustrating the protective system when it has been placed in its locked, safe position suitable for discarding.

The protective system of the invention includes a protective tubular sheath 10 which has an open first end, hereinafter termed an upper end 12, and a second or lower end 14 which has an opening 16 therethrough of limited size for a reason hereinafter explained. It should be pointed out that the tubular sheath 10 can be constructed of plastic, of glass or metal, but regardless of the material of construction, is preferably translucent or transparent with windows, so that the interior of the sheath is visible so graduation indicia on the syringe barrel can be read.

In the embodiments of the invention which are illustrated and described in the present application, the open upper end of the protective tubular sheath 10 carries a collar 20 which is fixed to the upper end 12 of the sheath in any suitable manner In other embodiments of the invention not here illustrated, the collar 20 can be formed integrally with the sheath 10, such as where the sheath and collar are both molded of plastic, or some other procedure is used to facilitate such unitary or integral construction. The collar 20 defines a radially inwardly extending annular rib or flange 22 and an internal shoulder 24, with an annular locking slot or groove 26 located therebetween. In the illustrated embodiments of the invention, the collar 20 defines an axially extending annular slot 27 into which the upper edge of the sheath is received. A beveled lip 29 defines the radially inner side of this slot.

Slidably and reciprocably disposed within the tubular sheath 10 for coaxial movement within the sheath is an elongated barrel 28 which is of hollow cylindrical construction. The cylindrical barrel 28 can be constructed of plastic or glass, and is typified by the types of construction conventionally used in present day medical syringes. The barrel 28 includes an open upper end 30 and a lower end portion 32. It is generally characteristic of the barrels included in the protective assemblies of the present invention that they are provided with an opening in the lower end portion of the barrel adequate to permit the ejection of the liquid therefrom, or the withdrawal of a body fluid thereinto, in the ordinary use and functioning of the barrel as a syringe for administering a hypodermic injection.

In the form of the invention which is here illustrated, the lower end portion 32 of the barrel 28 carries a generally frustoconically shaped end or closure plate 34 which terminates at its lower end or apex in a protuberant nipple or fluid ejection tip 36 of a conventional type well understood in the art. Secured to the nipple or tip 36 by frictional engagement is a hypodermic injection or fluid withdrawal device, such as a hypodermic needle 38. The interfitting relationship of the needle 38 to the barrel 28 is conventional and forms no part of the present invention.

At its upper end, the barrel 28 is provided with a radially outwardly projecting handle 40 which can be held between the forefinger and index finger when the protective assembly is in use. The handle 40 permits the barrel 28 to be retracted within the tubular sheath 10 at a later time during the use of the device in a manner and for a purpose hereinafter described. The handle 40 also allows the device to be utilized for administering a hypodermic injection of a liquid beneath the skin in the administration of medication, or to be used for the withdrawal of blood. The handle 40, when used in this respect, permits the barrel 28 to be held while a plunger, designated generally by reference numeral 42, is caused to undergo reciprocation relative to the barrel. The plunger 42 includes an elongated, cylindrical piston element 44 which fits snugly but movably within the barrel 28, and can be reciprocated within the barrel for the purpose of ejecting or withdrawing a liquid through the opening in the lower end thereof and through the hypodermic injection device or needle 38. The plunger 42 carries a disc-shaped thumb plate 46 at its upper end to permit it to be pressed with the thumb into the barrel 28 in a reciprocating motion at a time when the barrel is gripped between the forefinger and the index finger, using the handle 40.

The structure illustrated in FIGS. 1-3, and thus far described, is conventional and well understood in the art. The purpose of the present invention is to provide a syringe structure which can be used for its conventional purpose in the hands of a qualified and authorized person for performing a hypodermic operation, but which can then made absolutely safe for disposal with adequate safeguards and assurances against any possible reuse by unauthorized personnel who may retrieve the hypodermic injection device after it has been discarded. The risks attendant to such retrieval and re-use are well understood in connection with the role that such activity plays in drug abuse, or simply with respect to the inadvertent re-utilization of a syringe which may have been contaminated by prior use on another patient, unknown to medical personnel who might inadvertently then subsequently utilize it in the case of a second patient.

In order to provide the assurance against re-use which is a principal object of the present invention to achieve, a locking element is connected to the lower end of the barrel 28 and is designated generally by reference numeral 50. The locking element 50 includes a generally frustoconical cap plate 52 which is fitted against and secured to, the frustoconical closure plate 34 at the end of the barrel 28. At its outer periphery, the frustoconically shaped cap plate 52 carries a plurality of radially outwardly inclined and rearwardly bent fingers 54. The position of the fingers 54 is such that the fingers are located in a small annular space between the outer periphery of the barrel 28 and the inner surface of the sheath 10. The fingers 54 are made of spring metal so that they are continuously resiliently urged against the inside surface of the sheath 10 when the barrel 28 is reciprocated within the sheath. There is an inward loading of the fingers 54 in the radial direction so that the fingers are compressed inwardly against the resilient bias of the metal tending to cause the fingers to spring radially outwardly. Each of the fingers carries a small male protuberance 55 on the end portion thereof.

The locking element 50 functions in the manner best illustrated in FIG. 3. After the hypodermic injection has been administered, or blood withdrawal completed, and it is desired to render the device safe against subsequent use, the tubular sheath 10 is held while the handle 40 of the barrel 28 is used to retract the barrel into the sheath until it reaches the position shown in FIG. 3. At this time, the locking element 50 carried on the lower end of the barrel 28 functions to lock the barrel and the hypodermic injection device or needle 38 carried on the end thereof at the illustrated position within the protective tubular sheath 10.

The locking element 50 functions at this time by having the distended, radially projecting, rearwardly bent resilient fingers 54 slide past the flange 22 and then snap outwardly so that the male protuberances move into the female locking slot or groove 26 formed within the collar 20. The collar 20 is, of course, in one embodiment, secured to the upper end of the tubular sheath 10, or can be formed integrally therewith, and the locking of the barrel 28 at the illustrated position by means of the locking element 50 interengaging the locking slot 26 assures that the needle 38, and indeed the syringe which includes the barrel 28 and plunger 42, cannot be re-used. The device is now safe to discard and the possibilities of re-use are very substantially reduced. It is preferred, for some usages, to construct the tubular sheath 10 of a strong rigid material, such as a high density, relatively thick plastic, or even metal, so that it cannot be crushed or broken in order to gain access to the needle 38. It should also be pointed out that in some instances where, for example, a blood sample is to be withdrawn, the locking element 50 may simply be secured to the needle 38, and not to the barrel 28.

In FIGS. 4A-4C, a different embodiment of the invention is illustrated. For the reason that many of the parts shown in this embodiment are the same as the parts shown in FIGS. 1-3, identical reference numerals will be used for identifying these identical parts, and different and new reference numerals will be used only to identify parts which are different in the modified embodiment.

Referring initially to FIG. 4A, a syringe protective device in the form of the modified embodiment is there shown as the device appears at a time when it is being used for administering a hypodermic injection, or a withdrawal of body fluid. The tubular sheath 10 again contains the generally cylindrical and tubular barrel 28 which can be reciprocated within the tubular sheath after the syringe has been utilized. The tubular sheath 10 includes, as previously described, an open upper end 12 and a lower end portion 14 which defines a relatively small opening 16 which is of a size which is adequate for a portion of the hypodermic injection device or needle 38 to pass through in the manner hereinbefore described.

At its upper end, the tubular sheath 10 carries an annular collar 20 which, as previously explained, can be separately made in the manner illustrated in the drawing, or, with more expensive fabrication procedures, can be integrally formed with the tubular sheath 10, such as a mere extension of the remainder of the sheath. As in the prior embodiment, the annular collar 20 includes an annular flange or rib 22, and also defines a slot or groove between this rib and an internal shoulder 24. In the embodiment of the invention illustrated in FIGS. 4A-4C, however, instead of a locking slot of the type heretofore described as characterizing the embodiment shown in FIGS. 1-3 a differently configured locking slot 58 is illustrated. The locking slot 58 has a slight enlargement 58a adjacent its lower end in order to more easily accommodate a concavo-convex or bowed locking spring 60. The concavo-convex locking spring 60 has an upper end portion which bears against the shoulder 24, and at its lower end carries a reverse bent toe 60a. It will be perceived in referring to FIG. 4a that the bowed locking spring 60 is fitted within the locking slot 58 in a manner such that the convex side of the locking spring faces the outer surface of the barrel 28. In fact, it is preferred to have the bowed locking spring 60 contact the outer side of the barrel so as to perform a collateral function of guiding the barrel through its reciprocating movement within the tubular sheath. It will also be perceived in referring to FIG. 4A that the concave, radially outer side of the bowed locking spring 60 is spaced from the inner side of the locking slot 58 so that the locking spring can be forced into the intervening space and there accommodated when the locking of the barrel in a safe position is accomplished as hereinafter described.

A locking element is secured to the lower end of the barrel and is placed over, and secured to, the closure plate 34. The locking element is designated generally by reference numeral 64. The locking element 64 includes a frustoconical plate 66 which is centrally apertured to accommodate the extension of the nipple or spout therethrough. The frustoconical plate 66 extends outwardly to the outer peripheral edge of the frustoconical closure plate of the barrel 28, and is there secured to a peripheral, annular skirt 68 which projects axially along the outer periphery 28 for a short distance. The skirt portion 68 will be perceived to be of lesser thickness than the width of the annulus between the barrel 28 and the inner surface of the tubular sheath 10, and it will further be noted that the skirt 68 terminates in a beveled or tapered edge 70 at its upper end. At circumferentially spaced intervals around the outer side of the skirt 68 of the locking element 64, a plurality of wedge-shaped protuberances 72 are formed and project out and bear against the inner surface of the tubular sheath 10.

At a time when the usage of the syringe to administer a hypodermic injection has been completed, and it is desired to safely discard the syringe and the needle carried on the lower end thereof, the barrel 28 is again retracted into the tubular sheath 10 until the status depicted in FIG. 4C is achieved.

As the barrel 28 moves upwardly in the tubular sheath 10 as a result of holding the sheath in one hand and retracting the barrel by the use of the handle 40 with the other hand, the wedge-shaped protuberances 72 carried at circumferentially spaced intervals around the outer side of the skirt portion 68 will cause the bowed locking spring 60 to be forced outwardly within the locking slot 58. This movement will, in turn, cause the toes 58 carried thereon to spring inwardly to the position illustrated in FIG. 4C in which position they cannot pass by, but rather will bear against, the upper surface of the annular flange or rib 22. The barrel 28 of the syringe is now locked in this position, and the end of the syringe barrel through which the liquid is ejected, and the needle carried thereon, are both protectively hidden from view and locked in a physically protected position in which contact outside of the protective sheath is not possible. Discard of the device with a high assurance against unauthorized re-use is therefore possible at this time.

Figures 5A, 5B, 5C:
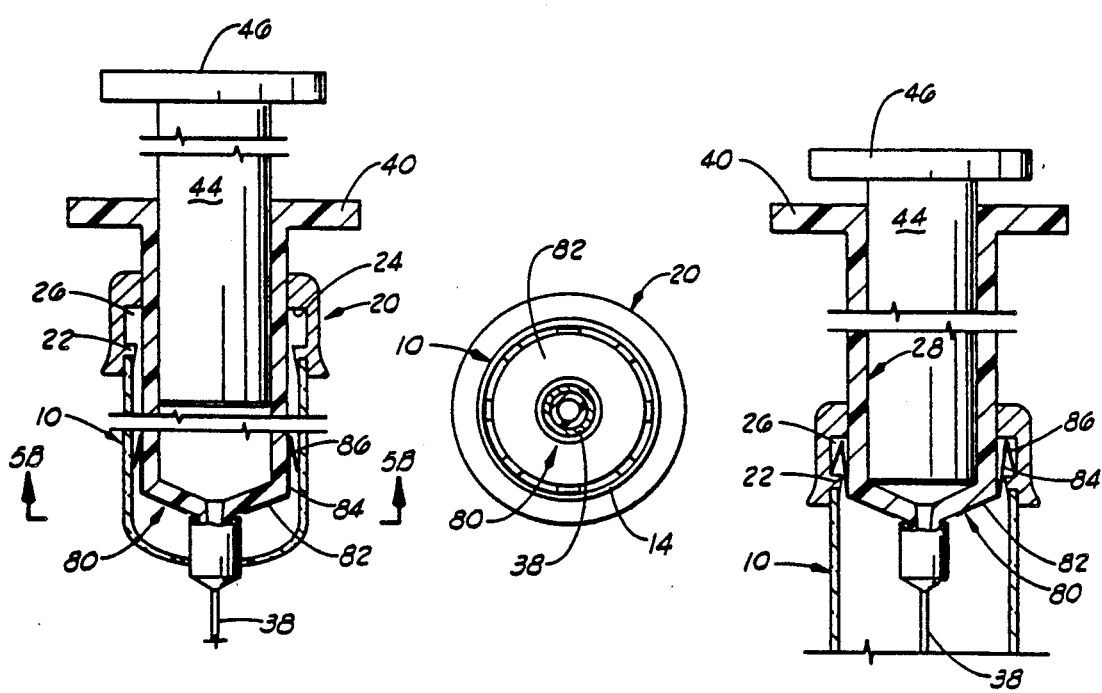
FIG. 5A is a partially sectional, partially elevational view similar to FIGS. 1 and 4A (with parts broken away), but illustrating yet a third embodiment of the invention.
FIG. 5B is a sectional view taken along line 5B—5B of FIG. 5A.
FIG. 5C illustrates the third embodiment of the protective system of the invention as it appears when the device has been shifted to its interlocking, safe status, and is ready to be discarded following use.

A third embodiment of the invention is illustrated in FIGS. 5A–5C. Again, like reference numerals have been utilized to denominate like parts. In the embodiment of the protective device depicted in these figures, a different locking element 80 is provided at the lower end of the barrel 28. The locking element 80 is constructed of spring metal, and includes a frustoconical cap plate 82 which is centrally apertured to accommodate the projection of the nipple or spout therethrough. The cap plate 82 is secured to the barrel at this location. The frustoconical cap plate 82 carries a peripheral, axially extending, generally cylindrical skirt 84 which projects closely adjacent the outer peripheral wall of the lower end of the barrel. Parts of the skirt 84 are then reverse bent to provide, at the axially upper end of the skirt, a series of locking flanges or tabs 86. These locking tabs 86 are resiliently deformed by the confining effect of the inner surface of the tubular sheath 10.

The locking tabs 86 are thus forced inwardly in resilient deformation so that, at a time when the barrel 28 is retracted upwardly within the tubular sheath 10 to the position illustrated in FIG. 5C, the locking flanges 86 snap outwardly into the locking slot or groove 26. When this action occurs, the lower end of the barrel 28 and/or the hypodermic needle 38 are protected and guarded by the surrounding protective tubular sheath 10 against inadvertent contact, and against re-use.

Although certain preferred embodiments of the invention have been herein described, it will be understood that various changes and innovations can be effected in the illustrated and described embodiments without departure from the basic principles upon which the invention is based. Changes and innovations of that type which thus do not depart from the basic principles of the invention are deemed to be circumscribed by the spirit and scope of the invention, and to be within the protection of the patent to be issued hereon, except insofar as such protection is precluded by any limits necessarily placed upon the construction and interpretation of the claims.

What is claimed is:

1. A protective assembly for preventing contact with the needle of a needle-carrying syringe used to perform hypodermic injections or to withdraw body fluids into the syringe comprising:
    elongated tubular protective sheath means including
        a tubular sheath having a first open end and having a second end defining an opening therethrough;
    a syringe device adapted for attachment of a hypodermic needle thereto, said syringe device comprising:
        a hollow cylindrical barrel extending through the first open end of said tubular sheath and slidably mounted coaxially within said sheath for relative axial movement between the barrel and said sheath, said hollow cylindrical barrel including:
        an open, plunger-receiving first end; and
        a second end portion having a tubular tip of reduced diameter relative to the diameter of the open, first end of said barrel, said second end portion of said barrel being located at least partially within said sheath, and said first end of said barrel being located outside of said sheath and spaced from said first open end of said sheath;
    a movable plunger projecting into the open, first end of said cylindrical barrel and fitting slidably within said barrel to function as a piston suitable for ejecting a fluid from said barrel through said tubular tip, or drawing a fluid through said tip into said barrel for sample taking purposes;
    locking means on the outer side of said barrel and around said tubular tip for cooperatively interlocking with said tubular sheath in a retracted position of the barrel in which said tubular tip is withdrawn within said sheath, and said barrel has been moved relatively from said second end of said sheath means toward said first open end thereof, said locking means slidably engaging said tubular sheath for slidably guiding the relative movement between said sheath and said barrel, said locking means on the outer side of said barrel and around said tip comprising:
        a plurality of radially deformable resilient fingers carried on said barrel at circumferentially spaced intervals around the outer periphery of the barrel, said fingers bearing resiliently against the inner surface of said sheath and being configured to facilitate reciprocating sliding movement of said barrel in said sheath by bearing against the interior of said tubular sheath, each of said radially deformable resilient fingers comprising a protuberant male locking end portion; and
    means on the tubular sheath adjacent its open end for interlocking with the resilient fingers of said locking means on the outer side of said barrel when said barrel is moved upwardly in said sheath to said retracted position, said interlocking means on said tubular sheath comprising at least one female opening for receiving the male locking end portion of at least one of said resilient fingers of said locking means.

2. The protective assembly of claim 1 wherein said female opening is a groove into which said protuberant male locking end portions of said resilient fingers snap to effect said interlocking.

3. The protective assembly of claim 1 wherein said locking means is a separate structural element from said barrel and from said tubular sheath.

4. A protective assembly for preventing contact with a needle used on a hypodermic syringe for injecting fluids into the body or for withdrawing fluids from the body comprising:
    an elongated tubular protective sheath means including a tubular sheath having a first open upper end and a second lower end portion having an opening therethrough;
    a hypodermic syringe device comprising:
        a hollow tubular barrel extending through the open first end of said tubular sheath and slidably mounted coaxially within said sheath for axial movement relatively between the barrel and said sheath, said barrel including:
        an open, plunger-receiving upper first end; and
        a second lower end portion having a tubular tip of reduced diameter relative to the first end of said barrel, said second end portion of said barrel being located predominantly within said sheath with the tip thereof aligned with the opening through the lower end portion of said tubular sheath whereby a needle carried thereon can project through, and move through, said opening, said first end of said barrel being located outside of said sheath and spaced from said open upper end of said sheath;

a movable plunger projecting into the open, first end of said tubular barrel and fitting slidably within said tubular barrel to function as a piston suitable for ejecting fluid from said barrel through said tubular tip, or for drawing fluid through said tubular tip into said barrel;

locking means on the outer side of said barrel around said tubular tip for cooperatively interlocking at least a portion of said hypodermic syringe device within said protective sheath in a retracted position in which said tubular tip is withdrawn within said sheath, and said barrel has been moved relatively axially within said sheath means further including:

a collar formed integrally with said sheath adjacent the open upper end thereof and guidingly contacting and engaging the outer periphery of said tubular barrel as said tubular barrel moves slidably and coaxially within said tubular sheath; and means carried on said tubular sheath adjacent the open upper end of said tubular sheath for interlocking with said locking means when said barrel is moved upwardly in said sheath means to said retracted position.

5. The protective assembly of claim 4 wherein said locking means comprises a plurality of radially deformable resilient fingers mounted adjacent the lower end portion of said barrel and bearing resiliently against the inner surface of said sheath, and each including a protuberant male locking end portion.

6. The protective assembly of claim 5 wherein said interlocking means carried on said tubular sheath comprises at least one female opening adjacent said collar for receiving at least one of said protuberant male locking end portions of two of said radially deformable resilient fingers.

7. The protective assembly of claim 4 wherein said locking means is a separate structural element from said barrel and from said tubular sheath.

* * * * *